US 12,241,884 B2

United States Patent
Campbell et al.

(10) Patent No.: US 12,241,884 B2
(45) Date of Patent: Mar. 4, 2025

(54) CHIP DETECTION SYSTEM FOR AN ENGINE FLUID SYSTEM

(71) Applicant: PRATT & WHITNEY CANADA CORP., Longueuil (CA)

(72) Inventors: Alexander Campbell, Mississauga (CA); Michael Paul Smith, Mississauga (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 119 days.

(21) Appl. No.: 18/303,964

(22) Filed: Apr. 20, 2023

(65) Prior Publication Data

US 2024/0353390 A1 Oct. 24, 2024

(51) Int. Cl.
*G01N 33/28* (2006.01)
*F16N 29/00* (2006.01)
*G01N 15/06* (2006.01)
*G01N 15/00* (2006.01)

(52) U.S. Cl.
CPC ......... *G01N 33/2858* (2013.01); *F16N 29/00* (2013.01); *G01N 15/0656* (2013.01); *F16N 2200/04* (2013.01); *F16N 2210/08* (2013.01); *G01N 2015/0053* (2013.01)

(58) Field of Classification Search
CPC .......... G01N 33/2858; G01N 15/0656; G01N 2015/0053; G01N 23/12; G01N 2223/205; G01N 33/2888; F16N 29/00; F16N 2200/04; F16N 2210/08
See application file for complete search history.

(56) References Cited

U.S. PATENT DOCUMENTS

| | | |
|---|---|---|
| 5,982,847 A | 11/1999 | Nelson |
| 8,559,006 B2 | 10/2013 | Penney et al. |
| 8,586,913 B2 | 11/2013 | Zhou et al. |
| 10,180,075 B1 * | 1/2019 | Andrus ............. G01N 33/2888 |
| 10,197,488 B2 | 2/2019 | Youssef |
| 10,705,038 B2 | 7/2020 | Ricci et al. |
| 10,866,201 B2 | 12/2020 | Best |
| 11,127,271 B2 | 9/2021 | Piech et al. |
| 11,250,681 B2 | 2/2022 | Shaw |

(Continued)

FOREIGN PATENT DOCUMENTS

WO 2018056950 3/2018

*Primary Examiner* — Alvaro E Fortich
(74) *Attorney, Agent, or Firm* — NORTON ROSE FULBRIGHT CANADA LLP

(57) ABSTRACT

A chip detection system for an engine fluid system includes an emitter located in a first position proximate to a fluid passage of the engine fluid system, the emitter including a radioactive source that generates ionizing radiation particles and transmits the ionizing radiation particles through a liquid within the fluid passage. A detector includes a detecting element located in a second position relative to the fluid passage with the liquid disposed between the emitter and the detector. The detecting element generates an electric current in response to the ionizing radiation particles contacting the detector. A controller is in communication with the detector to receive the electric current generated by the detecting element. The controller is operable to detect chips in the liquid when the electric current generated by the detecting element is greater than a threshold value of the electric current.

20 Claims, 5 Drawing Sheets

(56) References Cited

U.S. PATENT DOCUMENTS

| | | |
|---|---|---|
| 11,448,636 B2 | 9/2022 | Padilla et al. |
| 11,549,933 B2 | 1/2023 | Shenouda |
| 2003/0101801 A1 | 6/2003 | Wilson et al. |
| 2004/0213373 A1 | 10/2004 | Wilson et al. |
| 2011/0310391 A1* | 12/2011 | Janssen .................. G01N 21/85 356/438 |
| 2015/0082871 A1* | 3/2015 | Zha .................... G01N 33/2888 73/53.05 |
| 2016/0313237 A1* | 10/2016 | Young ...................... G06N 3/04 |
| 2018/0031504 A1* | 2/2018 | Ricci ................. G01N 33/2858 |

\* cited by examiner

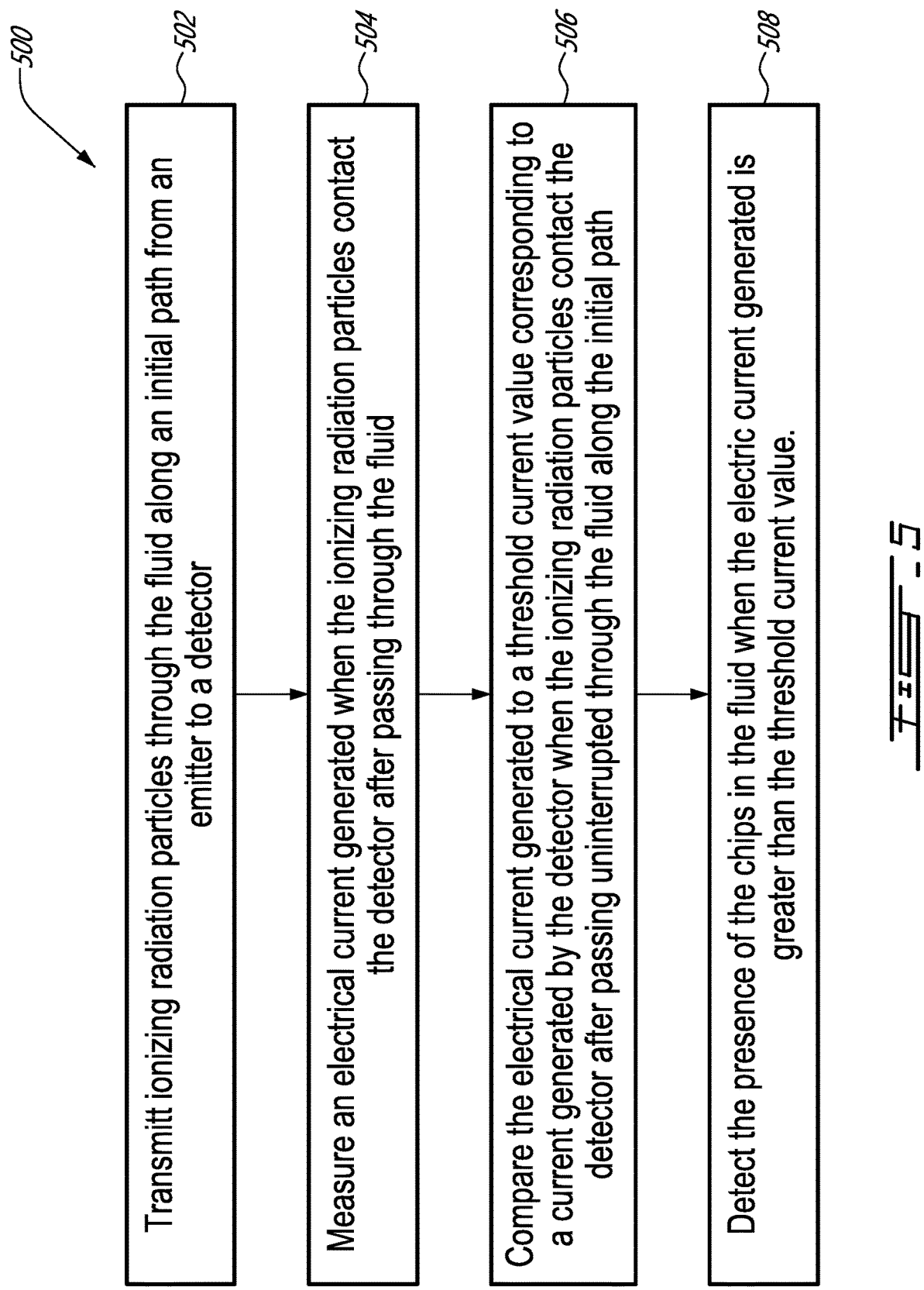

CHIP DETECTION SYSTEM FOR AN ENGINE FLUID SYSTEM

TECHNICAL FIELD

The present disclosure relates generally to the detection of chips or other physical debris in an engine fluid system, and more particularly to the detection of chips the oil system an engine.

BACKGROUND

Aircraft engines include oil systems used for cooling and lubrication. Because the oil flowing within such oil systems can collect and carry debris (e.g., "chips") from various mechanical components, the oil needs to be filtered. Oil filters are consumables and are replaced if significant quantities of chips are produced. As such, chip detection systems, or chip detectors, are sometimes used, which used to detect when the quantity of chips within the oil system exceeds an allowable level. Most existing oil system chip detectors are of a magnetic type, wherein a permanent magnet is used to collect ferrous chips within the oil system. The ferrous chips adhere to the detector and bridge an electric circuit, which can be observed by an indicator or detected by the engine control system to determine when the quantity of chips collected exceeds allowable levels.

These magnetic chip detectors tend to get clogged over time, and have to be regularly cleaned as part of a maintenance action. Therefore, while existing magnetic chip detectors are useful for their intended purpose, improvement is sought.

SUMMARY

There is accordingly provided a chip detection system for an engine fluid system, the chip detection system comprising: an emitter located in a first position proximate to a fluid passage of the engine fluid system, the emitter including a radioactive source that generates ionizing radiation particles and transmits the ionizing radiation particles through a liquid within the fluid passage; and a detector including a detecting element, the detecting element located in a second position relative to the fluid passage with the liquid disposed between the emitter and the detector, the detecting element generating an electric current in response to the ionizing radiation particles contacting the detector, and a controller in communication with the detector to receive the electric current generated by the detecting element, the controller operable to detect chips in the liquid when the electric current generated by the detecting element is greater than a threshold value of the electric current.

The chip detection system as defined above and described herein may further include one or more of the following features, in whole or in part, and in any combination.

In certain aspects, the emitter is located externally of the fluid passage on a first side thereof, and the detecting element is located on a second side of the fluid passage, substantially opposite the emitter.

In certain aspects, the emitter is oriented to transmit the ionizing radiation particles transversely through the fluid passage from the first side to the second side.

In certain aspects, the detecting element is dispensed radially outward of a wall of the fluid passage.

In certain aspects, the detecting element is a liner disposed along at least a portion of the fluid passage.

In certain aspects, the liner substantially fully surrounds the fluid passage, at least outside of a region thereof where the emitter is located.

In certain aspects, the liner extends about more than 270 degrees of a perimeter of the fluid passage, extending from a central portion of the liner directly opposite the emitter to remove outer ends of the liner located immediately adjacent the emitter.

In certain aspects, the detecting element is a liner that corresponds in shape to the fluid passage.

In certain aspects, the liner is arcuate and has an at least partially circular cross-sectional shape.

In certain aspects, the liner is located radially outward of the fluid passage.

In certain aspects, the detective element includes a resistive back plate, wherein the further away from the emitter the ionizing radiation particles contact the detective element, the smaller the current produced by the detective element.

In certain aspects, the emitter is located centrally within the fluid passage, the ionizing radiation particles being transmitted radially outwardly from the emitter.

There is further provided a method of detecting chips in a liquid flowing through a fluid passage of an engine fluid system, the method comprising: transmitting ionizing radiation particles through the liquid along an initial path from an emitter to a detector; measuring an electric current generated when the ionizing radiation particles contact the detector after passing through the liquid; comparing the current generated to a threshold value of the electric current, the threshold value of the electric current corresponding to a current generated by the detector when the ionizing radiation particles contact the detector after passing uninterrupted through the liquid along the initial path; and detecting chips in the liquid when the electric current generated is greater than the threshold value of the electric current.

The method as defined above and described herein may further include one or more of the following features, in whole or in part, and in any combination.

In certain aspects, the method includes using a resistive detection element to generate the electric current when the ionizing radiation particles contact the detector.

In certain aspects, the method includes generating the electric current using a liner that surrounds more than 50% of a perimeter of the fluid passage.

In certain aspects, the liner surrounds more than 270 degrees of the perimeter of the fluid passage.

In certain aspects, the method includes generating the electric current using a liner having a shape corresponding to that of the fluid passage.

In certain aspects, the method includes positioning the emitter and the detector diametrically opposite one another on opposite external sides of the fluid passage.

In certain aspects, the method includes transmitting the ionizing radiation particles transversely through the fluid passage.

In certain aspects, the method includes transmitting the ionizing radiation particles radially outwardly from the emitter, the emitter being located centrally within the fluid passage.

BRIEF DESCRIPTION OF THE DRAWINGS

Reference is now made to the accompanying figures in which:

FIG. 5 is a flow chart of a method for detecting chips in a liquid of engine fluid system, as described herein.

DETAILED DESCRIPTION

Figure 1:
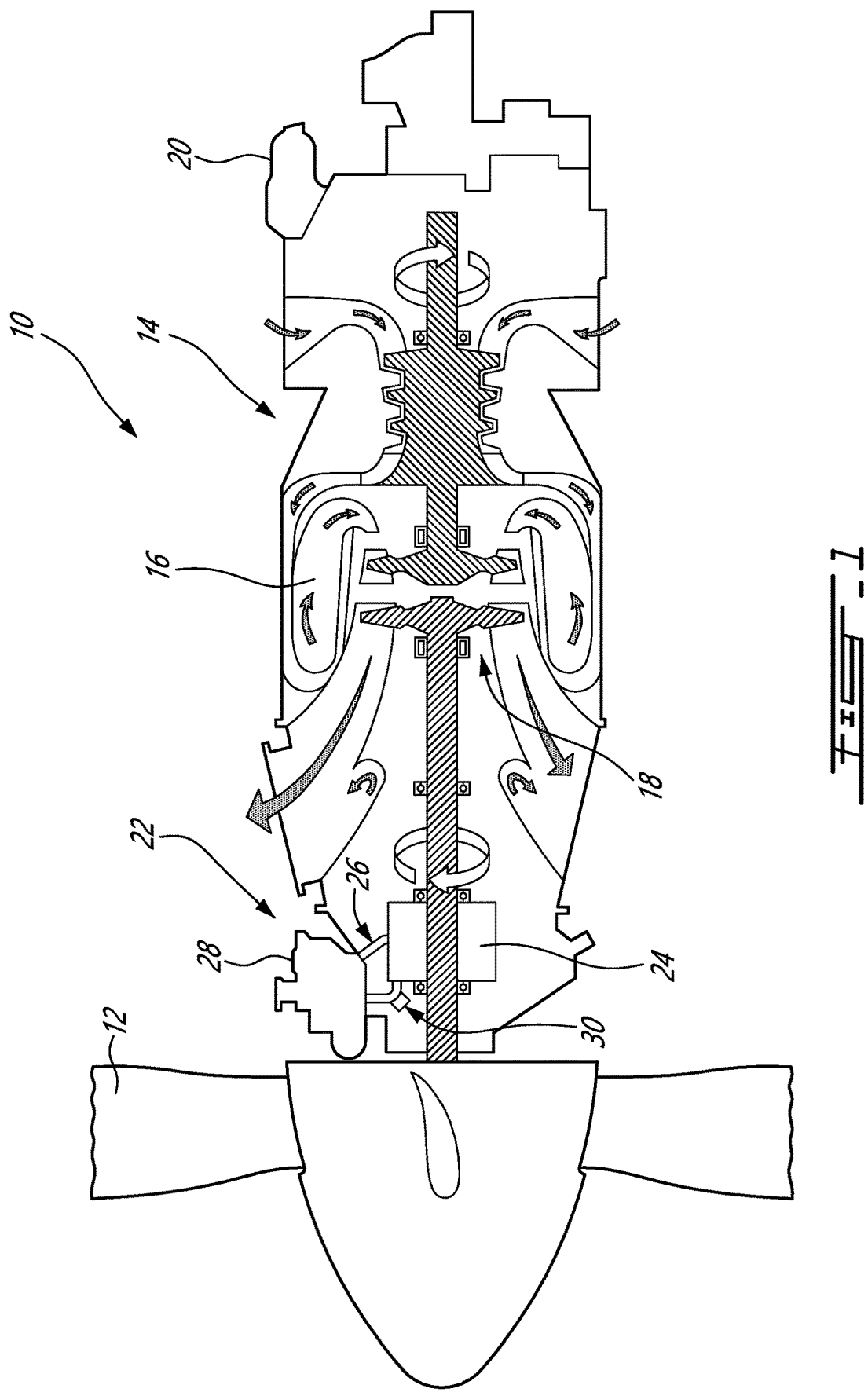
FIG. 1 is a schematic cross sectional view of an aircraft engine.

FIG. 1 illustrates an aircraft engine 10 (or simply "engine" 10, which in this exemplary embodiment is a turboprop gas turbine engine) of a type preferably provided for use in subsonic flight, generally comprising in serial flow communication a propeller 12 through which ambient air is propelled, a compressor section 14 for pressurizing the air, a combustor 16 in which the compressed air is mixed with fuel and ignited for generating an annular stream of hot combustion gases, and a turbine section 18 for extracting energy from the combustion gases. The engine 10 further includes an engine controller 20 for controlling flight parameters of the engine 10. The flight parameters may be, for instance, fuel flow regulation, thrust management, and actuation of valves and pumps required for proper operation of the engine 10.

Although the engine 10 as depicted in FIG. 1 is an aircraft engine, and more particularly a gas turbine engine, it is to be understood that the chip detection system as will be described herein can also be used within and/or in conjunction with other types of engines having an engine fluid system, for example automotive engines, marine engines, industrial or static gas turbine engines, power generation systems, other types of aerospace engines, and the like.

The engine 10 further includes a fluid system 22, operatively connected to one or more rotating components 24 of the engine 10. In accordance with one particular embodiment, the fluid system 22 is a blurbification system of the engine 10, and may therefore form part of an oil system of the engine. The fluid system 22 may therefore be refereed to herein as a lubricating system 22. The rotating components 24 may include, for instance, a gearbox 24 of the engine 10 and/or bearing cavities of the engine 10. The fluid system 22 includes a fluid circuitry 26, which in the context of a lubrication system will circulate a lubricant, such as oil, into and out of the gearbox 24, the bearing cavities of the engine and/or other components of the engine 10 requiring cooling and/or lubrication. In the embodiment shown, a pump 28 is used for circulating the lubricant within the fluid circuitry 26.

The engine 10 also includes a debris monitoring system 30, which will also be referred to herein as a chip detection system 30, that is operatively connected to the lubrication system 22 and is operable to detect the presence of debris (i.e., "chips") in the liquid medium (e.g., oil) of the lubrication system 22, as will be described in further detail below. The debris monitoring system 30 may be connected for example to the fluid circuitry 26 of the lubrication system 22. The lubricant debris monitoring system 30 may be configured for collecting debris within the lubricant and for collecting data about the quantity of debris within the lubricant.

Figure 2:
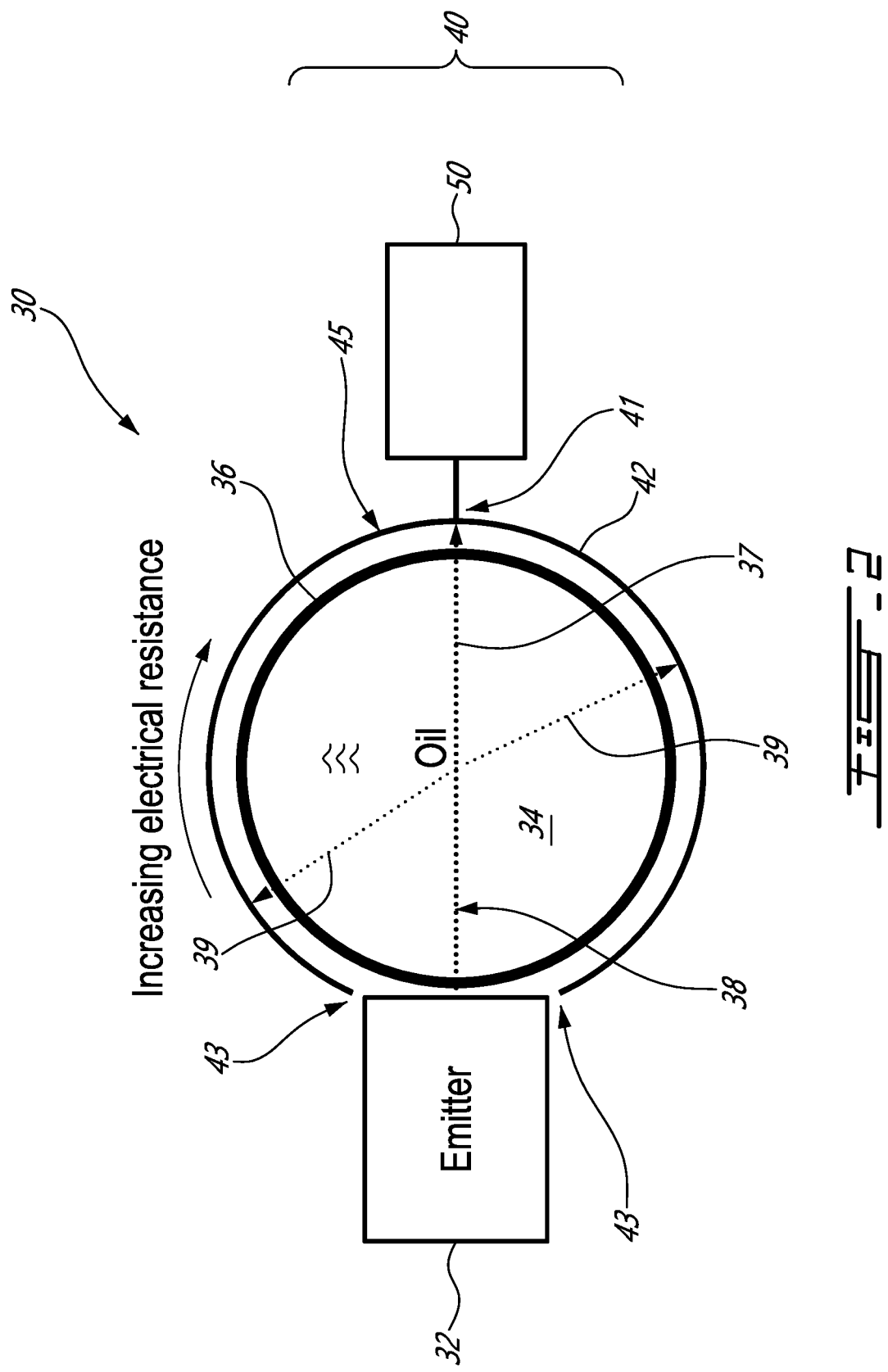
FIG. 2 is a schematic cross-sectional view of an ionizing chip detection system as described herein, for detecting chips within a fluid passage of the aircraft engine of FIG. 1.
Figure 3:
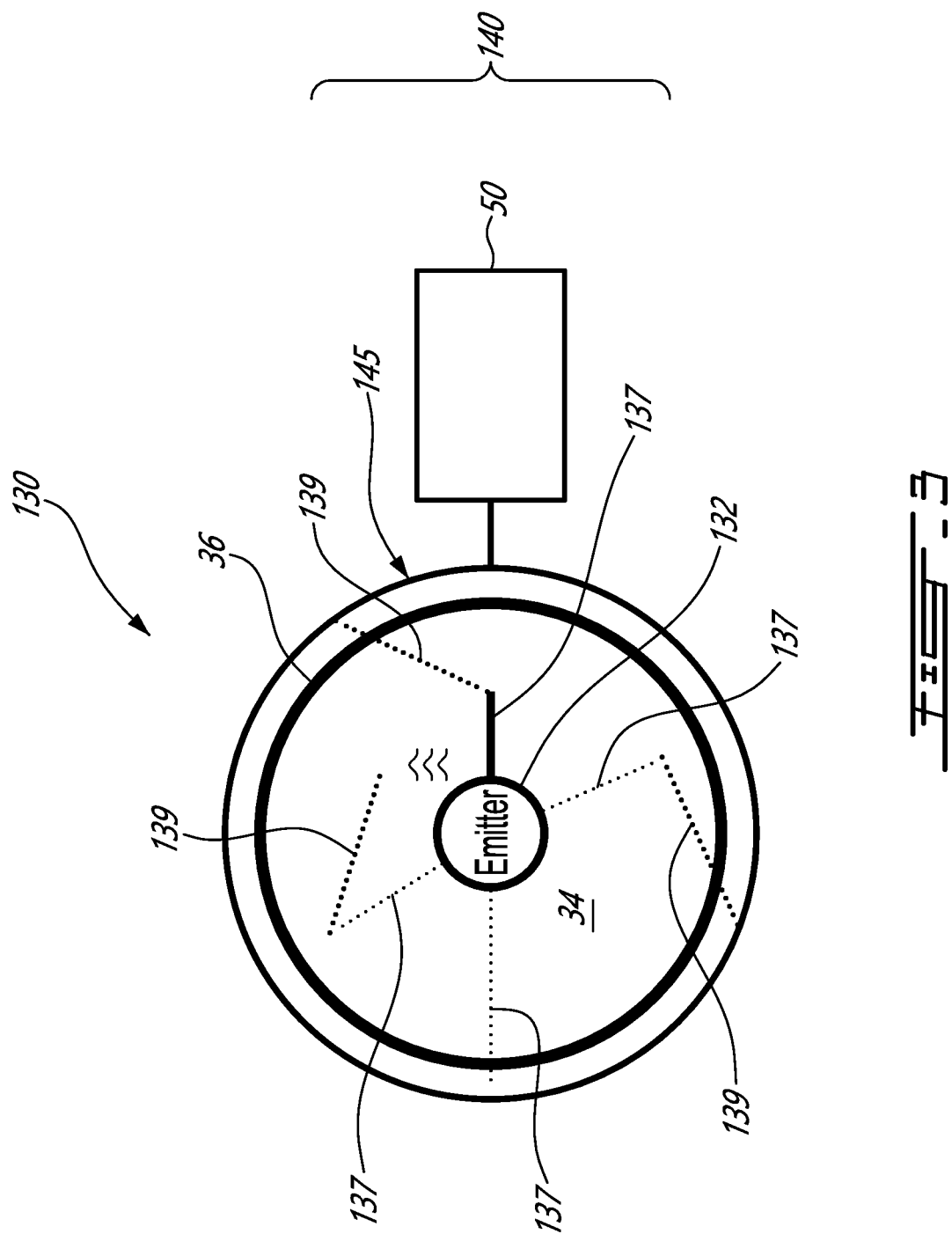
FIG. 3 is a schematic cross-sectional view of an ionizing chip detection system as described herein, for detecting chips within a fluid passage of the aircraft engine of FIG. 1.
Figure 4:
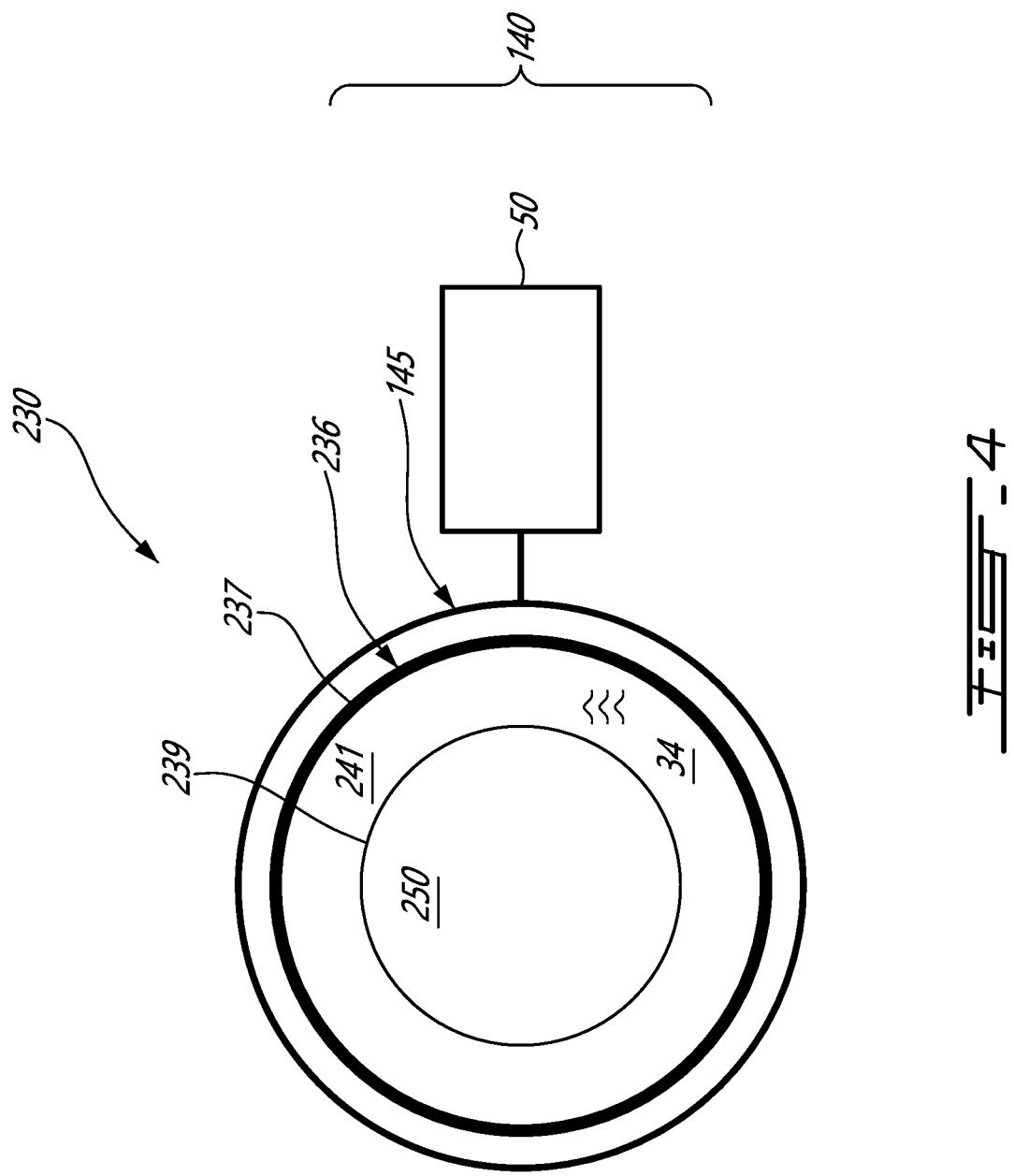
FIG. 4 is a schematic cross-sectional view of an ionizing chip detection system as described herein, for detecting chips within a fluid passage of the aircraft engine of FIG. 1.

Referring now to FIGS. 2-4, the chip detection system 30 of the engine 10 will now be described in further detail.

Referring now to FIG. 2, a schematic view of the chip detection system 30 in accordance with one embodiment is illustrated. As will be described, the chip detection system 30 uses ionizing radiation to detect chips and other debris within a liquid medium (or simply "liquid") 34 flowing within a fluid passage 36 of the fluid circuitry 26 in the fluid system 22 (e.g., a lubrication system) of the engine 10. In a particular embodiment, the liquid in question is oil and the lubrication system 22 is an oil system of the engine 10. The term "ionizing radiation" or "ionizing radiation particles" as used herein is understood to mean radiation consisting of particles having sufficient energy to cause ionization in the medium through which it passes. These ionizing radiation particles can include alpha particles, beta particles, gamma rays, X-rays and positrons, which will cause ionization in the fluid medium through which it passes.

The chip detection system 30 includes generally an emitter 32, having a radioactive source and which produces ionizing radiation particles 38, and a detector 40 adapted to receive the ionizing radiation particles 38 after they have passed through the liquid 34 within the fluid passage 36. In the manner described in further detail below, the detector 40 is operable to determine whether the ionizing radiation particles 38 have passed directly through the liquid 34 without being deflected by any chips within the liquid 34 (as schematically depicted by the transversely-extending path 37 in FIG. 2), or whether the ionizing radiation particles 38 have been deflected by chips within the liquid 34 (as schematically depicted using broken lines in FIG. 2 representing the deflected radiation paths 39).

More specifically, the emitter 32 of the chip detection system 30 emits low-radiation ionizing radiation particles 38 (for example, but not limited to, beta (B) particles) and transmits these ionizing radiation particles 38 through the liquid 34 within the fluid passage 36 in a first, emitted direction. In the depicted embodiment, the emitter 32 is located on a first side of the fluid passage 36 and is oriented such as to transmit the ionizing radiation particles 38 transversely through the fluid passage 36 from one side thereof to the other (left to right, in FIG. 2). However, it is to be understood that the emitter 32 may be placed elsewhere on or near the fluid passage 36, wherever it may be suitable in order to direct the flow of ionizing radiation particles 38 through the liquid (e.g., oil) that is to be monitored for the presence of chips. The emitter 32 is thus configured such as to direct a beam or flow of ionizing radiation particles 38 through the liquid 34 along a main emitted path 37. The radiation particles 38 will thus tend to follow this path 37, between the emitter 32 and the detector 40, unless they are deflected or scattered by chips within the liquid 34. The emitter 32 can be either passive (e.g., a passive radiation source that emits the ionizing radiation particles) or an active system which is controlled to emit ionizing radiation particles 38 as required. The chip detection system 30 may in certain embodiments therefore be a passive system, which provides its own excitation.

The detector 40 is positioned substantially opposite (e.g., diametrically opposite) to the emitter 32 on an opposite side of the fluid passage 36, generally in line with the main emitted path 37 of the ionizing radiation particles 38 that are emitted by the emitter 32, such as to receive (or capture) the ionizing radiation particles 38 after they have passed through the liquid 34 within the fluid passage 36. In the depicted embodiment, the detector 40 is located substantially opposite the emitter 32, for example on a second side of the fluid passage 36 with the emitter 32 located on a first side of the fluid passage 36.

The detector 40 includes a detecting element 45 in the form of a liner which is located outside (e.g., radially outward of) the fluid passage 36 (as shown in FIG. 2). Alternately, the detecting element 45 may be located on an inner surface of the wall of fluid passage 36, and thus may be directly exposed to the liquid 34. The detecting element 45 may simply be referred to herein as the "liner" 45, however it is to be understood that the detecting element 45 may also take other forms.

In certain embodiments, the liner 45 of the detector 40 has a shape which corresponds to that of the fluid passage 36. For example, in the embodiment of FIG. 2, the fluid passage 36 is tubular and has an at least partially circular cross-sectional shape, and therefore the liner 45 of detector 40 is arcuate and has a radius of curvature similar to that of the outer wall of the fluid passage 36. The liner 45 of the detector 40 extends at least partially around the fluid passage 36, extending away from a central portion 41 of the liner 45, defined at the location where the main path 37 of the ionizing radiation particles 38 impacts the detector 40 (at 3 o'clock in FIG. 2), towards remote outer ends 43 of the liner 45 which are circumferentially spaced apart from the central portion 41. In the embodiment of FIG. 2, the remote outer ends 43 of the liner 45 of the detector 40 are located proximate to, and on either side of, the emitter 32. In the embodiment of FIG. 2, the liner 45 of the detector 40 extends about more than 50% of the perimeter of the fluid passage. More particularly, the liner 45 extends more than ¾, or 270 degrees, of the perimeter of the fluid passage 36, extending from the central portion 41 opposite the emitter 32 to the remove outer ends 43 located immediately adjacent the emitter 32. Accordingly, the liner 45 of the detector 40 in this embodiment substantially fully surrounds the fluid passage 36, outside of the region where the emitter 32 is located. This will permit the detector 40 to detect not only the presence of chips within the liquid, which would be possible if the liner 45 of the detector 40 was only provided with the central portion 41 located at the point where the main path 37 of the ionizing radiation particles 38 impacts the detector 40, but also permits a quantity or level of chips present in the liquid to be detected as explained below.

The liner 45 of the detector 40 is operable to release electrons when it is exposed to the ionizing radiation particles 38 emitted by the emitter 32. These released electrons create a small electric potential difference (voltage). The detective element (or liner) 45 of the detector 40 is a resistive detection element, having for example a resistive back plate 42, wherein the further along the resistive back plate 42 electrons travel, the greater the resistance and thus the smaller the current when compared with that portion or those portions of the liner 45 that are closer to the emitter 32.

In other words, if the ionizing radiation particles 38 impact the liner 45 of the detector 40 at points thereon closer to the emitter 32 and thus closer to the remote outer ends 43 of the liner 45 (which will tend to occur if the ionizing radiation particles 38 are scattered by chips in the liquid resulting in the deflected radiation paths 39), then the greater the current produced by the liner 45 and measured by a controller 50 in communication with the liner 45, either direction or via a suitable electric circuit (which may either form part of the controller 50 or the detector itself). Conversely, if little to no scatter of the ionizing radiation particles 38 occurs and the ionizing radiation particles 38 follow the main path 37 and impact the liner 45 at or near the central portion 41 thereof, the greater the electric resistance and thus the smaller the current produced by the liner 45 and measured by the controller 50. In the depicted embodiment, the controller 50 forms part of the chip detection system 30 and is in communication with the detector 40 thereof. In other embodiments, the controller 50 may instead be integrated into a main engine controller, such as a full authority digital engine controller (FADEC) for example. In all cases, however, the controller 50 remains in communication with the detector 40 as described herein, as well as the emitter 32 when necessary, for the purposes of controlling operation of the chip detection system 30.

As such, if ionizing radiation particles 38 interact with one or more chips (or other debris) within the liquid 34, the ionizing radiation particles 38 emitted into the liquid by the emitter 32 will scatter, and be redirected along deflected paths 39 for example. This scattering results in ionizing radiation particles 38 interacting with the detector 40 closer to the emitter 32 and, consequently, an increased current will be produced by the detector 40 (because of the reduced electric resistance in the resistive back plate 42 closer to the emitter 32). This increased current is measured by the controller 50 which is in electric communication with the liner 45 of the detector 40. The current produced by the detector 40 may be conditioned and amplified by an electric circuit, either within the controller 50 or separate therefrom, as required, and is used by the chip detection system 30 to determine the presence of chips within the liquid. The greater the current produced by the detector 40 and measured by the controller 50 of the chip detection system 30, the greater the number and/or size of chips within the liquid.

Referring now to FIG. 3, a schematic view of a chip detection system 130 in accordance with another embodiment is illustrated. The chip detection system 130 is similar to the chip detection system 30 of FIG. 2 as described above, with like reference numerals referring to like components, but with certain differences as will be explained. The emitter 132 of the chip detection system 130 is located internally within the fluid passage 36, rather than being located on an external side of the passage. As such, in the embodiment of FIG. 3 the emitter 132 is located centrally within the fluid passage 36 such that the liquid 34 within the fluid passage 36 flows around the emitter 132. The emitter 132 is capable of emitting ionizing radiation particles 38 is several different radial directions, for example along multiple radially-extending paths 137. The ionizing radiation particles 38 are therefore emitted radially outwardly, along these radially-extending paths 137. If the ionizing radiation particles 38 emitted by the emitter 132 come into contact with a chip within the liquid 34, they will be deflected or scattered and thus will change trajectory—leading to deflected radiation paths 139. The detector 140 of the chip detection system 130 includes a liner 145 that at least partially surrounds the fluid passage 36 and may, in certain embodiments, extend circumferentially about a full perimeter of the fluid passage 36 and thus may be annular in shape.

The liner 145 of the detector 140 need not be a resistive element, as per the detector 40 described above. Rather, the liner 145 of the detector 140 can rely on absorption of the ionizing radiation particles 38 to detect the presence of chips within the liquid 34 of the fluid passage 36. Scattered radiation (along scattered radiation paths 139) from the emitter 132 will result in longer transmission paths before the ionizing radiation particles 38 reach the surrounding liner 145 of the detector 140. When the ionizing radiation particles 38 come into contact with chips within the liquid 34 and consequently scatter, the path between the emitter 132 and liner 145 of the detector 140 is increased, thereby reducing the quantity of ionizing radiation particles 38 that reach the liner 145 and consequently increasing the current measured by the detector 140. This increased current measured by the controller 50 in communication with the liner 145 of the detector 140, caused by the reduced number of ionizing radiation particles 38 that reach the liner 145, indicates the presence of chips in the liquid 34.

It is to be understood that the chip detection system 30, with the offset emitter 32 rather than the central emitter 132, may also employ such an absorption style system wherein a resistive detecting element is not necessary. Instead, the detector 40 of the chip detection system 30 may similarly use The configuration of the chip detection system 130, with the emitter 132 being located centrally within the fluid passage 36, permits the liquid 34 within the fluid passage 36 to be used as a shielding medium for the ionizing radiation particles 38.

Referring now to FIG. 4, a schematic view of a chip detection system 230 in accordance with another embodiment is illustrated. The chip detection system 230 is similar to the chip detection system 130 of FIG. 3 as described above, with like reference numerals referring to like components, but with certain differences as will be explained. The chip detection system 230 may be particularly useful for larger diameter fluid passages. A fluid passage 236 includes a radially outer wall 237 and a radially inner wall 239 that define therebetween a generally annular internal conduit 241 through which the liquid 34 flows. Consequently, a large central cavity 250 is defined radially inward of the radially inner wall 239. Within this central cavity 250, either of the chip detection system 30 or the chip detection system 130 can be disposed, thereby making the fluid passage 236 a dual-flow passage, within an inner fluid passage (e.g., fluid passage 36) and a radially outer, and annular, fluid passage 236. The emitter used in the chip detection system 230 may therefore be a central, absorption type emitter 132 as used in the chip detection system 130, or an emitter 32 as used in the chip detection system 30 but simply placed internally within the cavity 250. The detector 140 used in the chip detection system 230 will be the same as that of the chip detection system 130. Alternately, any of the above detectors can be placed directly inside the fluid flow path itself, which also allows the liquid 34 to be used as shielding for the emitted radiation.

Referring to FIG. 5, a method 500 of detecting chips in a fluid of a fluid system in an aircraft engine, such as the lubrication system 22 of the aircraft engine 10 described above, is depicted. The method 500 includes a step 502 of transmitting the ionizing radiation particles 38 through the liquid 34 along an initial path 37, 137 from an emitter 32, 132, to a detector 40, 140. At step 504, an electric current is measured, the electric current being generated when the ionizing radiation particles 38 contact the detector 40, 140 after passing through the liquid 34. At step 506, the electric current generated is then compared to a threshold value of the electric current, the threshold value of the electric current corresponding to a current generated by the detector 40, 140 when the ionizing radiation particles 38 contact the detector after passing uninterrupted through the liquid 34 along the initial path 37, 137. At step 508, the presence of the chips in the liquid 34 is detected when the electric current generated is greater than the threshold value of the electric current.

The chip detection systems 30, 130, 230 as described herein may also be said to provide a chip detector that comprises an ionizing radiation source (emitter 32, 132) and a detector 40, 140. The emitter emits ionizing radiation that is either absorbed, scattered or passes through the liquid medium (e.g., oil). The presence of chips in the oil affects the amount of radiation that reaches the detector and where upon the detector it reaches. This is used to indicate the presence of chips in the oil.

The embodiments described in this document provide non-limiting examples of possible implementations of the present technology. Upon review of the present disclosure, a person of ordinary skill in the art will recognize that changes may be made to the embodiments described herein without departing from the scope of the present technology. For example, although the fluid passage 36 of the fluid system 22 is generally described above in the context of an oil tube or oil passage of an oil system of the engine 10, it is to be understood that the fluid passage 36 may include other liquid-carrying passage within the engine 10, including for example a channel, tube, coupling, orifice or other conduit within which the liquid, which is to be monitored for chips, flows during operation of the engine 10. Yet further modifications could be implemented by a person of ordinary skill in the art in view of the present disclosure, which modifications would be within the scope of the present technology.

The invention claimed is:

1. A chip detection system for an engine fluid system, the chip detection system comprising:
   an emitter located in a first position proximate to a fluid passage of the engine fluid system, the emitter including a radioactive source that generates ionizing radiation particles and transmits the ionizing radiation particles through a liquid within the fluid passage; and
   a detector including a detecting element, the detecting element located in a second position relative to the fluid passage with the liquid disposed between the emitter and the detector, the detecting element generating an electric current in response to the ionizing radiation particles contacting the detector, and
   a controller in communication with the detector to receive the electric current generated by the detecting element, the controller operable to detect chips in the liquid when the electric current generated by the detecting element is greater than a threshold value of the electric current.

2. The chip detection system as defined in claim 1, wherein the emitter is located externally of the fluid passage on a first side thereof, and the detecting element is located on a second side of the fluid passage, substantially opposite the emitter.

3. The chip detection system as defined in claim 2, wherein the emitter is oriented to transmit the ionizing radiation particles transversely through the fluid passage from the first side to the second side.

4. The chip detection system as defined in claim 2, wherein the detecting element is dispensed radially outward of a wall of the fluid passage.

5. The chip detection system as defined in claim 1, wherein the detecting element is a liner disposed along at least a portion of the fluid passage.

6. The chip detection system as defined in claim 5, wherein the liner substantially fully surrounds the fluid passage, at least outside of a region thereof where the emitter is located.

7. The chip detection system as defined in claim 5, wherein the liner extends about more than 270 degrees of a perimeter of the fluid passage, extending from a central portion of the liner directly opposite the emitter to remove outer ends of the liner located immediately adjacent the emitter.

8. The chip detection system as defined in claim 1, wherein the detecting element is a liner that corresponds in shape to the fluid passage.

9. The chip detection system as defined in claim 6, wherein the liner is arcuate and has an at least partially circular cross-sectional shape.

10. The chip detection system as defined in claim 6, wherein the liner is located radially outward of the fluid passage.

11. The chip detection system as defined in claim 1, wherein the detective element includes a resistive back plate, wherein the further away from the emitter the ionizing radiation particles contact the detective element, the smaller the current produced by the detective element.

12. The chip detection system as defined in claim 1, wherein the emitter is located centrally within the fluid passage, the ionizing radiation particles being transmitted radially outwardly from the emitter.

13. A method of detecting chips in a liquid flowing through a fluid passage of an engine fluid system, the method comprising:

transmitting ionizing radiation particles through the liquid along an initial path from an emitter to a detector;

measuring an electric current generated when the ionizing radiation particles contact the detector after passing through the liquid;

comparing the current generated to a threshold value of the electric current, the threshold value of the electric current corresponding to a current generated by the detector when the ionizing radiation particles contact the detector after passing uninterrupted through the liquid along the initial path; and detecting chips in the liquid when the electric current generated is greater than the threshold value of the electric current.

14. The method of claim 13, further comprising using a resistive detection element to generate the electric current when the ionizing radiation particles contact the detector.

15. The method of claim 13, further comprising generating the electric current using a liner that surrounds more than 50% of a perimeter of the fluid passage.

16. The method of claim 15, wherein the liner surrounds more than 270 degrees of the perimeter of the fluid passage.

17. The method of claim 13, further comprising generating the electric current using a liner having a shape corresponding to that of the fluid passage.

18. The method of claim 13, further comprising positioning the emitter and the detector diametrically opposite one another on opposite external sides of the fluid passage.

19. The method of claim 18, further comprising transmitting the ionizing radiation particles transversely through the fluid passage.

20. The method of claim 13, further comprising transmitting the ionizing radiation particles radially outwardly from the emitter, the emitter being located centrally within the fluid passage.

\* \* \* \* \*